United States Patent [19]

Nishimura et al.

[11] Patent Number: 4,808,746

[45] Date of Patent: Feb. 28, 1989

[54] PREPARATION OF TRIFLUOROMETHYLBENZONITRILE FROM TRIFLUOROMETHYLBENZALDEHYDE

[75] Inventors: Yasunobu Nishimura, Kamifukuoka; Toshikazu Kawai, Kawagoe; Yoshikazu Sugimori, Kamifukuoka, all of Japan

[73] Assignee: Central Glass Company, Limited, Ube, Japan

[21] Appl. No.: 129,309

[22] Filed: Dec. 7, 1987

[30] Foreign Application Priority Data

Dec. 8, 1986 [JP] Japan ................................ 61-290393

[51] Int. Cl.$^4$ ............................................. C07C 120/00
[52] U.S. Cl. ........................................................ 558/314
[58] Field of Search ............................................ 558/314

[56] References Cited

U.S. PATENT DOCUMENTS 4,211,721  7/1980  Cotter ................................. 558/343
4,235,807  11/1980  Fuhlhage ........................... 558/314
4,456,562  6/1984  Tamura et al. ..................... 558/314

FOREIGN PATENT DOCUMENTS 2214061  9/1973  Fed. Rep. of Germany .
2550262  5/1977  Fed. Rep. of Germany .

OTHER PUBLICATIONS

Hunt, Chemistry & Industry, Nov. 1961, p. 1873.
"A Convenient One-step conversion of Aldehydes into Nitriles", by T. van Es., J. Chem Soc., (1965) p. 1564.

Primary Examiner—Joseph Paul Brust
Attorney, Agent, or Firm—Fleit, Jacobson, Cohn & Price

[57] ABSTRACT

In preparing trifluoromethylbenzonitrile by reaction of trifluoromethylbenzaldehyde with hydroxylamine, the rate of reaction is enhanced and formation of trifluoromethylbenzamide is suppressed by carrying out the reaction in an organic solvent which is immiscible with water and has a sufficiently high boiling point, e.g. nitrotoluene, and continuously distilling by-produced water from the reaction system. The solvent can easily and almost entirely be recovered and reused.

7 Claims, No Drawings

PREPARATION OF TRIFLUOROMETHYLBENZONITRILE FROM TRIFLUOROMETHYLBENZALDEHYDE

BACKGROUND OF THE INVENTION

This invention relates to a method of preparing trifluoromethylbenzonitrile (abbreviated to TFMBN) from trifluoromethylbenzaldehyde.

TFMBN is useful as an intermediate material of some medicines including tranquilizer and agricultural chemicals and also as an intermediate material of a certain type of liquid crystal.

U.S. Pat. No. 4,211,721 shows obtaining TFMBN by cyanizing chlorobenzotrifluoride, but this method is not suited to industrial practice because of using a highly toxic cyanide. DE-A No. 2,214,061 shows preparing TFMBN by fluorinating α,α,α-trichlorotolunitrile, but this fluorination reaction is difficult to complete so that the reaction product contains difluoro matter. DE-A No. 2,550,262 shows preparing TFMBN by reaction of trichloromethylbenzotrifluoride with ammonia, but the yield of the aimed compound is low: for example, less than 15% in the case of preparing 4-trifluoromethylbenzonitrile. Besides, in any of these methods complicated operations are needed for post-reaction treatment.

In general, as reported in J. Chem. Soc., (1965) 1564, nitriles can be prepared directly from aldehydes at fairly good yields by refluxing a solution of an aldehyde in formic acid with hydroxylamine. However, this method involves several problems from a practical point of view. First, recovery of formic acid is troublesome because the acid is diluted with by-produced water. Furthermore, the report mentions that the nitriles were isolated by diluting the reaction liquid with water. If the formic acid as diluted is reused in the reaction of the next batch the rate of reaction becomes very low. When this method is used for preparing TFMBN from trifluoromethylbenzaldehyde there arises another problem that isolation of the formed TFMBN is difficult because TFMBN and formic acid form an azeotrope. Besides, when brought into contact with water TFMBN relatively easily hydrolyzes into trifluoromethylbenzamide by reason of the electron effect of its trifluoromethyl group.

SUMMARY OF THE INVENTION

It is an object of the present invention to provide an industrially practicable method for preparing trifluoromethylbenzonitrile with high efficiency.

The method according to the invention is for preparing trifluoromethylbenzonitrile (TFMBN) by reaction of trifluoromethylbenzaldehyde (TFMBA) with hydroxylamine at an elevated temperature and is characterized in that the reaction is carried out in an organic solvent, which is immiscible with water and has a boiling point higher than the boiling point of TFMBN to be formed, and that water formed by the reaction is substantially continuously distilled out of the reaction system.

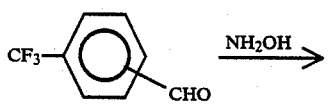

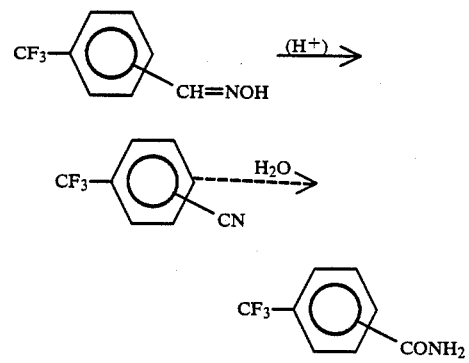

As represented by the above reaction formula, the reaction betweem TFMBA and hydroxylamine forms trifluoromethylbenzaldoxime as an intermediate, and dehydration of this aldoxime gives TFMBN. We have discovered that the both stages of the reaction proceed smoothly and rapidly when the reaction is carried out in an organic solvent which is immiscible with water and has a sufficiently high boiling point, such as nitrotoluene for instance, while continuously dissipating by-produced and evaporated water from the reaction system. The dissipation of water is effective also for suppression of hydrolysis of TFMBN (indicated in the above reaction formula by arrow in broken line) into trifluoromethylbenzamide. Also it is an advantage of the method according to the invention that TFMBN as the reaction product can easily be isolated by distillation. Besides, most of the high boiling point solvent is recovered as the residue of the distillation and, as recovered, can be reused for the reaction of a next batch. Therefore, this method is very favorable for industrial preparation of TFMBN.

DESCRIPTION OF THE PREFERRED EMBODIMENTS

In this invention it is essential to use, as a liquid medium for the reaction, an organic solvent which is immiscible with water and has a boiling point far higher than 100° C. and higher than the boiling point of TFMBN to be formed. Good examples of such solvents are nitrobenzene, nitrotoluene, chloronitrobenzene and diphenyl ether. The quantity of the high boiling point organic solvent is at least 30 parts by weight, and is preferably 100–400 parts by weight, per 100 parts by weight of TFMBA subjected to reaction.

At an initial stage of the reaction to form TFMBN the reaction system is kept heated at approximately 100° C., and the temperature is gradually raised as the vapor of by-produced water is continuously dissipated from the reaction system. Ultimately the reaction system may be heated up to about 200° C., but it is preferable to limit the ultimate temperature within the range from about 140° C. to about 160° C. As the temperature of the reaction system is raised above 100° C. by removing water, the dehydration reaction of intermediately formed trifluoromethylbenzaloxime to form TFMBN is further promoted.

In this method it suffices to use 1.0–1.2 mol of hydroxylamine per mol of TFMBA, but there arises no problem by using a larger quantity of hydroxylamine. In industrial practice it is usual to use hydroxylamine in the form of an acid salt such as hydrochloride or sulfate.

Therefore, there is the need of using a base as an auxiliary material for neutralizing purpose. Usually an organic acid salt such as, for example, sodium formate or sodium acetate is used as the base, though it is also possible to use an inorganic base such as sodium hydroxide or potassium hydroxide.

To further promote dehydration reaction of trifluoromethylbenzaldoxime formed as intermediate, it is optional and rather desirable to add a suitable organic acid or anhydride such as formic acid, acetic acid or acetic anhydride to the starting materials. The quantity of such an organic acid or anhydride is not strictly limited and may be roughly equivalent to the quantity of TFMBA by mol.

The invention is further illustrated by the following nonlimitative examples.

EXAMPLE 1

A reactor having a capacity of 100 liters was charged with 50.0 kg of 2-nitrotoluene, and in this solvent 25.0 kg of 4-trifluoromethylbenzaldehyde, 14.2 kg of hydroxylamine sulfate, 11.7 kg of sodium formate and 7.8 kg of 80% formic acid were subjected to reaction. Initially the reaction system was heated to 100° C., and water formed by the reaction was continuously distilled out of the reactor. The temperature of the reaction system was gradually raised up to 140° C., and at this temperature stirring was continued for 3 hr. By this operation the conversion of 4-TFMBA reached 99.6%, and selectivity to 4-trifluoromethylbenzonitrile was 90.5%. The water dissipated from the reactor during the above operation amounted to 9.8 kg, and the reaction product included 8.4% of 4-trifluoromethylbenzamide.

Then the whole quantity of the reaction liquid was distilled to collect organic matter. After washing with water the organic matter was distilled to isolate 4-TFMBN as distillate. As the result 20.0 kg (yield 81.6%) of 4-TFMBN was obtained. From the residue of distillation 47.8 kg of 2-nitrotoluene was recovered, which means 95.6% recovery. The recovered solvent was used in repeating the reaction to form 4-TFMBN, and the object was well accomplished without problem.

EXAMPLE 2

A reactor having a capacity of 1 liter was charged with 500 g of 4-chloronitrobenzene, and in this solvent 250 g of 2-trifluoromethylbenzaldehyde, 120 g of hydroxylamine hydrochloride, 172 g of 40% aqueous solution of sodium hydroxide and 104 g of acetic acid were subjected to reaction. Initially the reaction system was heated to 100° C., and water formed by the reaction was continuously distilled out of the reactor. The temperature of the reaction system was gradually raised up to 140° C., and at this temperature stirring was continued for 4 hr. By this operation the conversion of 2-TFMBA reached 97.3%, and selectivity to 2-trifluoromethylbenzonitrile was 89.6%. The water dissipated from the reactor during the above operation amounted to 202 g, and the reaction product included 7.7% of 2-trifluoromethylbenzamide.

Then the reaction liquid was filtered to remove solid salts, and the liquid distilled out of the reactor during the above operation was added to the filtrate. The mixed liquid was washed with water and distilled to isolate 2-TFMBN as distillate. As the result 203.8 g (yield 83.0%) of 2-TFMBN was obtained. From the residue of distillation 482.5 g of 4-chloronitrobenzene was recovered, which means 96.5% recovery. The recovered solvent was used in repeating the reaction to form 2-TFMBN, and the object was well accomplished without problem.

EXAMPLE 3

A reactor having a capacity of 100 ml was charged with 50.0 g of 2-nitrotoluene, and in this solvent 25.0 g of 3-trifluoromethylbenzaldehyde, 14.2 g of hydroxylamine sulfate, 11.7 g of sodium formate and 7.8 9 of 80% formic acid were subjected to reaction. Initially the reaction system was heated to 100° C. and water formed by the reaction was continuously distilled out of the reactor. The temperature of the reaction system was gradually raised up to 140° C., and at this temperature stirring was continued for 4 hr. By this operation the conversion of 3-TFMBA reached 99.5%, and selectivity to 3-trifluoromethylbenzonitrile was 92.1%. The water dissipated from the reactor during the above operation amounted to 10.3 g, and the reaction product included 6.8% of 3-trifluoromethylbenzamide.

Then the reaction liquid was filtered to remove solid salts, and the liquid distilled out of the reactor during the above operation was added to the filtrate. The mixed liquid was washed with water and distilled to isolate 3-TFMBN as distillate. As the result 21.5 g (yield 87.5%) of 3-TFMBN was obtained. From the residue of distillation 47.7 9 of 2-nitrotoluene was recovered, which means 95.4% recovery. The recovered solvent was used in repeating the reaction to form 3-TFMBN, and the object was well accomplished without problem.

COMPARATIVE EXAMPLE

In a reactor having a capacity of 1 liter, a mixture of 500 g of 2-nitrotoluene, 250 g of 4-TFMBA, 142 g of hydroxylamine sulfate, 117 g of sodium formate and 78 g of 80% formic acid was subjected to reaction by refluxing at 107° C. without removing water formed by the reaction. After continuing refluxing for 5 hr the reaction liquid was analyzed. The conversion of 4-TFMBA had reached 96.9%, but selectivity to 4-TFMBN was only 56.8%. The reaction product included 16.8% of 4-trifluoromethylbenzaloxime and 23.6% of 4-trifluoromethylbenzamide.

Comparing such results with the results obtained in Example 1 it is evident that dissipation of the by-produced water from the reaction system is very effective for promotion of conversion of the intermediately formed aldoxime into the nitrile and also for suppression of the hydrolysis of the nitrile.

What is claimed is:

1. A method of preparing trifluoromethylbenzonitrile by reaction of trifluoromethylbenzaldehyde with hydroxylamine at an elevated temperature,
    characterized in that said reaction is carried out in an organic solvent selected from the group consisting of nitrobenzene, nitrotoluene, chloronitrobenzene and diphenyl ether, and that water formed by the reaction is substantially continuously distilled out of the reaction system,
    wherein, said organic solvent is used in an amount of 30 to 400 parts by weight per 100 parts by weight of said trifluoromethylbenzaldehyde, and
    wherein, the temperature of the reaction system is gradually raised as water is dissipated, the maximum temperature of the reaction system being not higher than 200° C.

2. A method according to claim 1, wherein the maximum temperature of the reaction system is in the range from about 140° C. to about 160° C.

3. A method according to claim 1, wherein said reaction is carried out in the presence of a member selected from the group consisting of formic acid, acetic acid and acetic anhydride.

4. A method according to claim 1, wherein said trifluoromethylbenzaldehyde is 2-trifluoromethylbenzaldehyde.

5. A method according to claim 1, wherein said trifluoromethylbenzaldehyde is 3-trifluoromethylbenzaldehyde.

6. A method according to claim 1, wherein said trifluoromethylbenzaldehyde is 4-trifluoromethylbenzaldehyde.

7. The process of claim 1 wherein the source of hydroxylamine is an acid salt of hydroxylamine selected from the group consisting of hydroxylamine sulfate and hydroxylamine hydrochloride, said acid salt of hydroxylamine being used together with a base.

* * * * *